US00PP25932P3

(12) United States Plant Patent
Danziger

(10) Patent No.: US PP25,932 P3
(45) Date of Patent: Sep. 22, 2015

(54) ***PETUNIA* PLANT NAMED 'DCAS298'**

(50) Latin Name: *Petunia sensu wijsman*
Varietal Denomination: DCAS298

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 0 days.

(21) Appl. No.: 13/986,310

(22) Filed: Apr. 18, 2013

(65) Prior Publication Data

US 2014/0317815 P1 Oct. 23, 2014

(51) Int. Cl.
*A01H 5/02* (2006.01)

(52) U.S. Cl.
USPC ..... Plt./356.18
CPC ..... *A01H 5/02* (2013.01)

(58) Field of Classification Search
USPC ..... Plt./356.18
See application file for complete search history.

(56) References Cited

PUBLICATIONS

CPVO, 2013.*
LVG Heidelberg, 2012.*

* cited by examiner

*Primary Examiner* — Keith Robinson
(74) *Attorney, Agent, or Firm* — Cassandra Bright

(57) ABSTRACT

A new and distinct *Petunia* cultivar named 'DCAS298' is disclosed, characterized by large flowers colored dark purple with an ivory rim. The new variety is vigorous and very well branched. Plants flower abundantly and have a mounded, trailing shape. The new variety is a *Petunia*, normally produced as an outdoor garden or container plant.

2 Drawing Sheets

Figure 1:
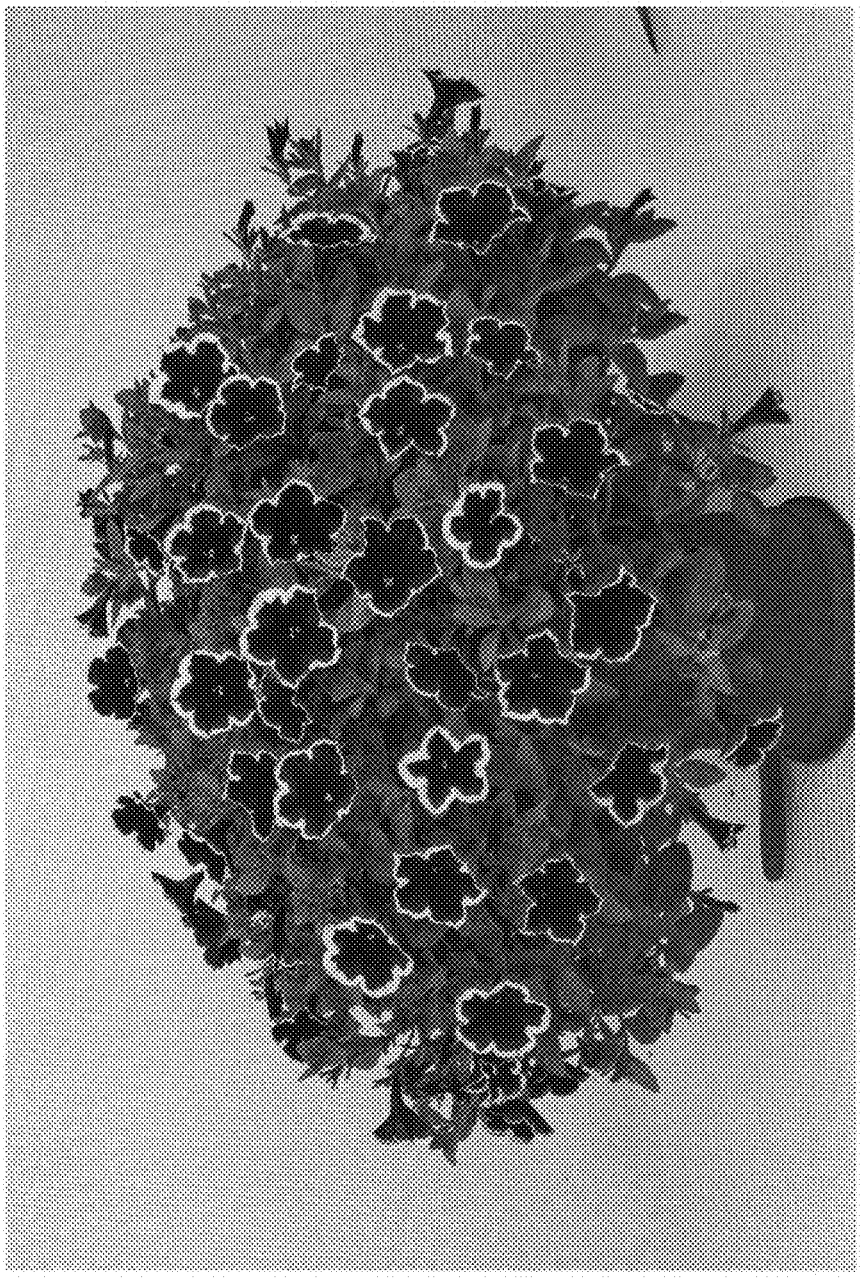

Latin name of the genus and species: *Petunia sensu wijsman.*

Variety denomination:
'DCAS298'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during December of 2010.

The seed parent is the unpatented commercial seedling variety referred to as *Petunia* '10-4241'. The pollen parent is the unpatented seedling variety referred to as *Petunia* '10-4179', containing the black gene described in utility U.S. Pat. No. 7,642,436. The new variety was discovered in August of 2011 by the inventor in a group of seedlings resulting from the 2010 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in September of 2011 and has shown that the unique features of this cultivar are stable and reproduced true to type in more than 25 generations.

SUMMARY OF THE INVENTION

The cultivar 'DCAS298' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCAS298' These characteristics in combination distinguish 'DCAS298' as a new and distinct *Petunia* cultivar:

1. Mounded and trailing plant shape.
2. Vigorous and very branched plant.
3. Flower color is dark purple with ivory rim.
4. Flower size is large.
5. Abundant flowering.

Plants of the new cultivar 'DCAS298' are similar to plants of the seed parent, *Petunia* '10-4241' in most horticultural characteristics, however, plants of the new cultivar 'DCAS298' are larger with more branches per plant than the seed parent. Flowers of 'DCAS298' are larger than flowers of the seed parent, and more flowers are produced per plant. The flower color of the new variety is dark purple flowers with an ivory colored rim compared to blue flowers with a white rim flowers of the seed parent. Additionally, 'DCAS298' produces a mounded, trailing plant habit compared to the semi upright plant habit of '10-4241'.

Plants of the new cultivar 'DCAS298' are similar to plants of the pollen parent; *Petunia* '10-4179' in most horticultural characteristics, however, plants of the new cultivar 'DCAS298' are larger, with more branches per plant than the pollen parent. 'DCAS298' also produces an abundant quantity of dark purple flowers with an ivory colored rim compared to the medium quantity of dark purple flowers with white stripes of the pollen parent. Additionally 'DCAS298' produces a mounded trailing plant habit compared to the trailing plant habit of '10-4179'.

COMMERCIAL COMPARISON

Plants of the new cultivar 'DCAS298' are comparable to the variety *Petunia* 'Balpephan' U.S. Plant Pat. No. 22,440, and which contains utility U.S. Pat. No. 7,642,436. The two *Petunia* varieties are similar in most horticultural characteristics; however, the new variety 'DCAS298' differs in producing dark purple flowers with an ivory colored rim compared to the purple flowers with wide yellow stripes of the comparator 'Balpephan'. Additionally 'DCAS298' produces a mounded-trailing and very well branched plant form compared to the mounded and lesser branched form of comparator 'Balpephan'. Additionally 'DCAS298' produces flowers with a flat interior aspect, compared to the curved, rolled floral interior of comparator 'Balpephan'.

Plants of the new cultivar 'DCAS298' can also be compared to the commercial variety *Petunia* 'Balpepin' U.S. Plant Pat. No. 22,414, U.S. Pat. No. 7,642,436. These varieties are similar in most horticultural characteristics; however 'DCAS298' produces smaller dark purple flowers with an ivory colored rim compared to the larger purple with yellowish-white striped flowers of comparator 'Balpepin'. 'DCAS298' produces a plant with medium width leaves compared to the wide leaves of comparator 'Balpepin'. Additionally 'DCAS298' produces a mounded-trailing and very well branched plant form compared to the semi-upright and moderately branched form of comparator 'Balpepin'.

BRIEF DESCRIPTION OF THE PHOTOGRAPHS

The accompanying photograph in FIG. 1 illustrates in full color a typical plant of 'DCAS298' grown in a greenhouse, in a 13 cm pot. Age of the plant photographed is approximately 3 months from a rooted cutting.

Figure 2:
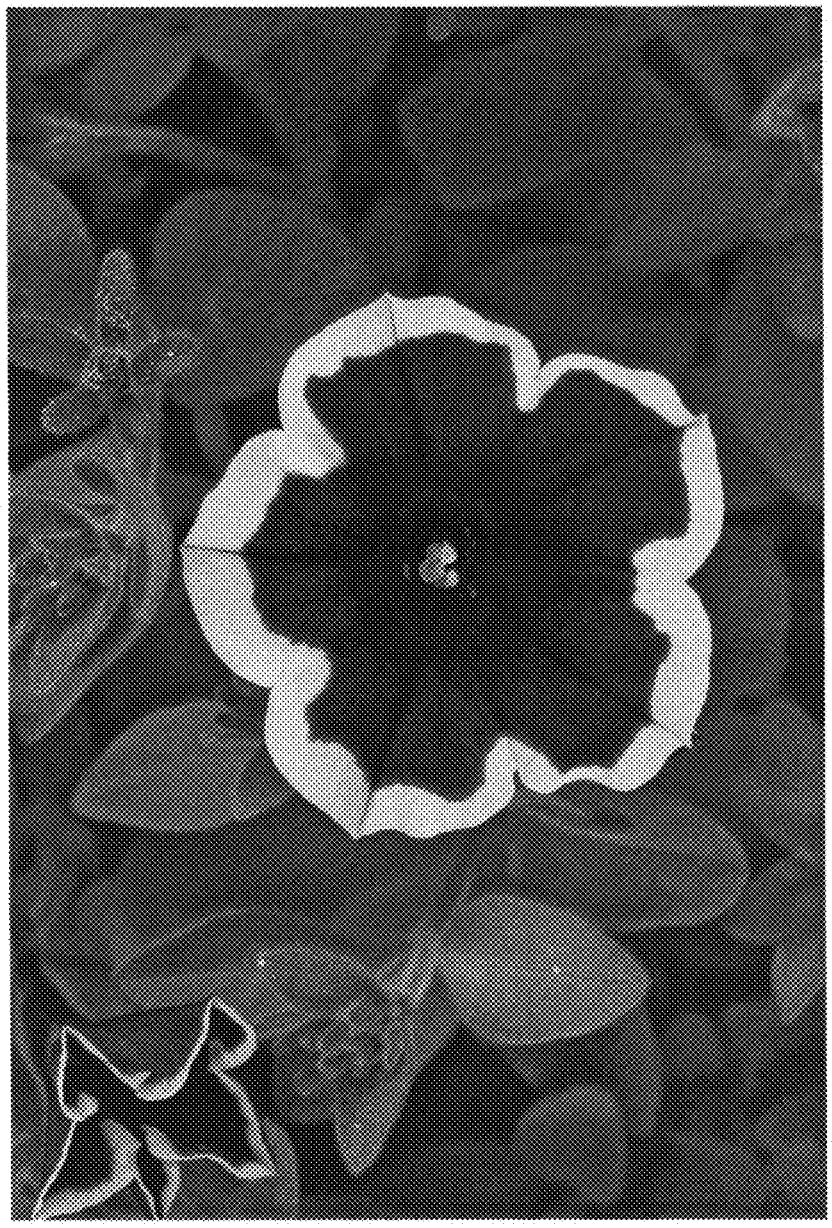

FIG. 2 illustrates in full color a close up of a typical bloom of 'DCAS298'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCAS298' plants grown outdoors during, Spring, Summer, and Autumn in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DCAS298'.

PROPAGATION

Time to initiate roots: About 10 to 14 days.
Root description: Fibrous.

PLANT

Age of plant described: Approximately 60 days from rooted cutting.
Pot size of plant described: 13 cm.
Growth habit: Mounded.
Height: Approximately 15 cm.
Plant spread: Approximately 60 cm.
Growth rate: Vigorous.
Branching characteristics: Very Branched.
Quantity of primary lateral branches: 8.
Characteristics of primary lateral branches:
- *Form*.—Cylindrical.
- *Length*.—50 cm.
- *Diameter*.—About 0.4 cm.
- *Color*.—Yellow-green group 144C RHS.
- *Texture*.—Pubescent.
- *Strength*.—Good.

Internode length: About 2.5 cm.

FOLIAGE

Leaf:
- *Arrangement*.—Opposite.
- *Quantity*.—Approximately 20 per branch.
- *Average length*.—6.0 cm.
- *Average width*.—2.0 cm.
- *Shape of blade*.—Elliptic.
- *Apex*.—Acute.
- *Base*.—Acute.
- *Margin*.—Entire.
- *Texture of top surface*.—Velvety, pubescent.
- *Texture of bottom surface*.—Velvety, pubescent.
- *Aspect*.—90°.
- *Foliage variegation*.—None.
- *Foliage blistering*.—None.
- *Color*.—Young foliage upper side: Yellow-green group 146B RHS. Young foliage under side: Yellow-green group 146C RHS. Mature foliage upper side: Yellow-green group 146A RHS. Mature foliage under side: Yellow-green group 146B RHS.
- *Venation*.—Type: Pinnate. Venation color upper side: Yellow-green group 146B RHS. Venation color under side: Yellow-green group 146C RHS.
- *Petiole*.—Length: About 1 cm. Diameter: About 0.4 cm. Color: Yellow-green group 146A RHS. Texture: Velvety.

FLOWER

Natural flowering season: Spring, Summer & Autumn in Moshav Mishmar Hashiva, Israel.
Days to flowering from rooted cutting: About 30 days.
Inflorescence and flower type and habit: Axillary, single flower, salverform shape, Erect outwardly facing habit.
Rate of flower opening: 2 to 3 days from bud to fully opened flower.
Flower longevity on plant: 3 to 6 days.
Approximate quantity of flowers per plant: About 90.
Persistent or self-cleaning: Self-Cleaning.
Bud:
- *Shape*.—Tubular.
- *Length*.—About 3.5 cm.
- *Diameter*.—About 0.6 cm.
- *Color*.—Violet-blue group N92A RHS.

Flower size:
- *Diameter*.—About 5.5 cm.
- *Length*.—About 2.5 cm.
- *Flower tube diameter at distal end*.—1.1 cm.
- *Flower tube diameter at proximal end*.—0.3 cm.

Petals:

*Length from throat*.—About 2 cm.

*Width*.—About 2.5 cm.

*Quantity*.—5.

*Texture*.—Velvety.

*Apex*.—Acute.

*Margin*.—Entire.

*Color*.—When opening: Upper surface: Violet-blue group N92A RHS. Lower surface: Purple group 79B RHS. Fully opened: Upper surface: Purple group 79A RHS. Lower surface: Purple group 79B RHS. Flower throat (inside): Purple group N79A RHS. Flower throat, vein: Purple group N79A RHS. Flower tube (outside): Purple group N79B RHS. Flower tube, vein: Purple group N79A RHS. Fading: Petals fading to: Violet-blue group N92B RHS, not fading.

Flower rim coloration: The ivory colored rim width is usually about 3-4 mm. However some flowers on same plant may have a wider rim of 6-10 mm. Color is Green-yellow group 1D RHS at all stages.

Calyx/sepals:

*Quantity per flower*.—5.

*Shape*.—Elliptic.

*Length*.—About 1 cm.

*Width*.—About 0.3 cm.

*Apex*.—Rounded.

*Base*.—Cuneate.

*Margin*.—Entire.

*Texture*.—Velvety.

*Color*.—Upper Surface: Yellow-green group 146A RHS. Lower Surface: Yellow-green group 146B RHS.

Peduncle:

*Length*.—About 3 cm.

*Diameter*.—About 0.1 cm.

*Color*.—Yellow-green group 146B RHS.

*Orientation*.—45°.

Fragrance: None.

REPRODUCTIVE ORGANS

Stamens:

*Number*.—5.

*Filament length*.—About 2 cm.

Anthers:

*Shape*.—Rounded.

*Length*.—About 0.2 cm.

*Color*.—Yellow group 2D RHS.

Pollen:

*Color*.—Yellow group 2D RHS.

*Quantity*.—Much.

Pistil:

*Number*.—1.

*Length*.—About 2.2 cm.

*Style*.—Length: About 2.6 cm. Color: Green-yellow 1C.

*Stigma*.—Shape: Rounded. Color: Yellow-green group 154A RHS. Ovary Color: Yellow-green group 144B RHS.

OTHER CHARACTERISTICS

Seeds and fruits: About 50 Brown 200B, round seeds of about 0.5 mm diameter, per one Brown 200C conical capsule.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates temperatures between 5° to 40° C.

What is claimed is:

1. A new and distinct cultivar of *Petunia* plant named 'DCAS298' as herein illustrated and described.

* * * * *